US005496367A

United States Patent [19]

Fisher

[11] Patent Number: 5,496,367

[45] Date of Patent: Mar. 5, 1996

[54] BREAST IMPLANT WITH BAFFLES

[76] Inventor: Jack Fisher, 5884 Fredricksburg, Nashville, Tenn. 37215

[21] Appl. No.: 189,123

[22] Filed: Jan. 27, 1994

Related U.S. Application Data

[63] Continuation of Ser. No. 4,187, Jan. 13, 1993, abandoned.

[51] Int. Cl.$^6$ .......... A61F 2/12

[52] U.S. Cl. .......... 623/8

[58] Field of Search .......... 623/7, 8

[56] References Cited

U.S. PATENT DOCUMENTS

| | | | |
|---|---|---|---|
| 3,559,214 | 2/1971 | Pangman | 623/8 |
| 3,934,274 | 1/1976 | Hartley, Jr. | 623/8 |
| 4,205,401 | 6/1980 | Frisch | 623/8 |
| 4,298,998 | 11/1981 | Naficy | 623/8 |
| 4,433,440 | 2/1984 | Cohen | 623/8 |
| 4,605,412 | 8/1986 | LaForest et al. | 623/8 |
| 4,650,487 | 3/1987 | Chaglassian | 623/8 |
| 4,676,795 | 6/1987 | Grundei | 623/8 |
| 4,685,447 | 8/1987 | Iverson et al. | 623/8 |
| 4,790,848 | 12/1988 | Cronin | 623/8 |
| 4,995,882 | 2/1991 | Destouet et al. | 623/8 |
| 5,147,398 | 9/1992 | Lynn et al. | 623/8 |
| 5,171,269 | 12/1992 | Bark | 623/7 |
| 5,246,454 | 9/1993 | Peterson | 623/7 |
| 5,383,929 | 1/1995 | Ledergerber | 623/8 |

*Primary Examiner*—Randy C. Shay
*Attorney, Agent, or Firm*—Michael G. Petit

[57] ABSTRACT

A breast implant with baffles includes an elastomeric envelope adapted to contain a fluid material and baffles inside the envelope to reduce or dampen wave or ripple action and motion of the fluid material contained by the envelope when implanted in a breast.

2 Claims, 1 Drawing Sheet

2
16
10
18
18
18"
11
20
18'
12
14
22
2
13

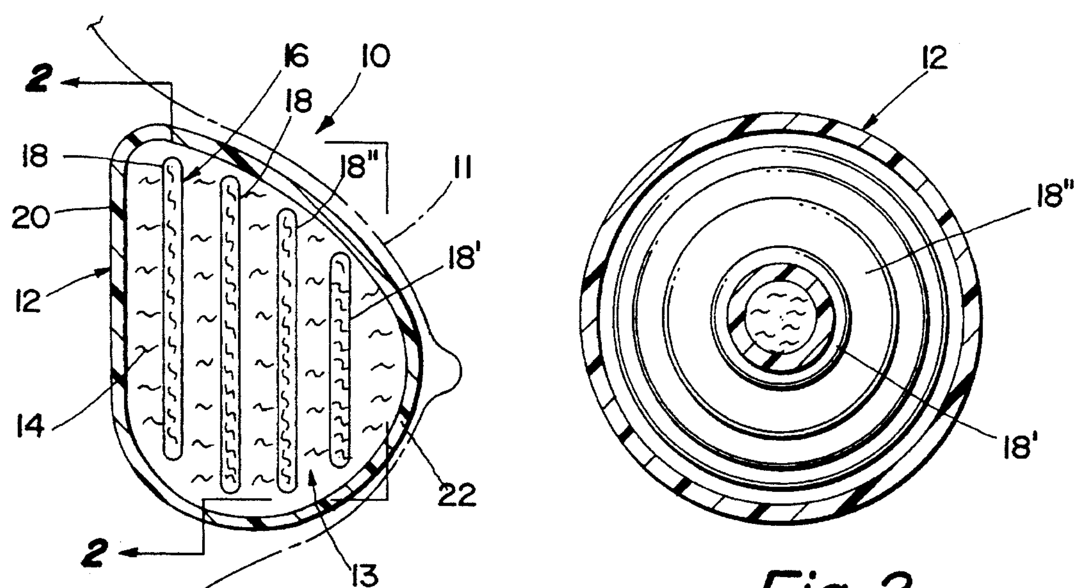
Fig. 1
Fig. 2
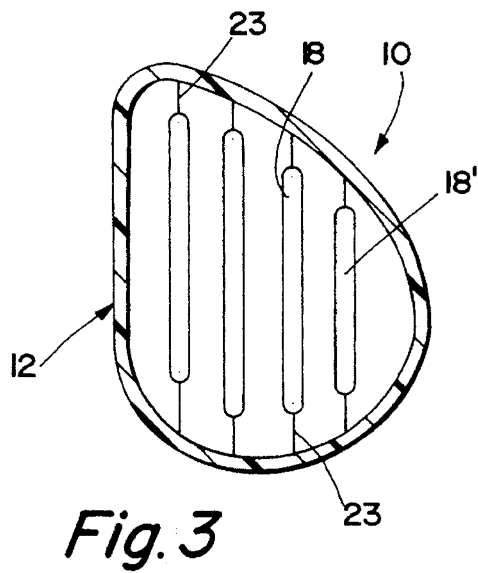
Fig. 3
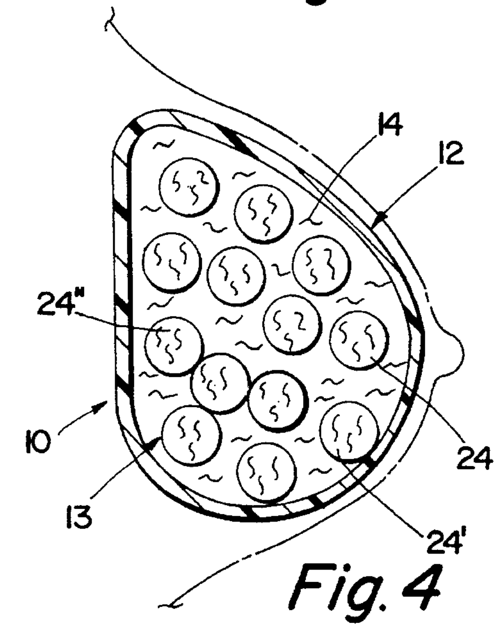
Fig. 4
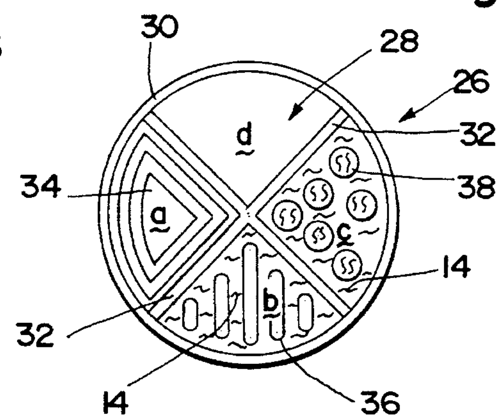
Fig. 5

BREAST IMPLANT WITH BAFFLES

CROSS REFERENCE TO RELATED APPLICATIONS

This is a continuation of application Ser. No. 08/004,187; filed Jan. 13, 1993, now abandoned.

FIELD OF THE INVENTION

The present invention relates generally to fluid filled implants and, more particularly, to fluid filled breast implants.

BACKGROUND OF THE INVENTION

A known problem with breast implants which are filled with fluid material, particularly fluid material of relatively low viscosity such as saline, is a tendency of the fluid-filled envelope of the implant to deform as a result of motion of the fluid in the envelope. Furthermore, wave and ripple action of the fluid within the envelope is often visible through the overlying tissue of the breast. These problems detract from the natural appearance of a reconstructed or enhanced breast. An implanted envelope may also encounter problems due to formation of scar tissue around the implant if the material within the envelope does not sufficiently resist deformation of the envelope.

Attempts to eliminate these problems, which are most prevalent with implanted envelopes containing fluid of relatively low viscosity such as saline, have included the use of multiple lumens within the envelope. This approach, however, does not eliminate the necessity to use a fluid or gel of relatively higher viscosity in one or more of the multiple lumens to give structural shape and the desired density and resiliency to the implant. Also, multi-lumen implants do not eliminate entirely the wave/ripple motion problem, particularly in those lumens filled with a relatively low viscosity fluid.

SUMMARY OF THE INVENTION

The present invention is a baffled breast implant which includes baffles within an envelope which reduce or eliminate undesired wave or ripple motion of fluid material contained in the envelope and may act to maintain the shape of the implant consistent with the contours of the baffles.

In accordance with one aspect of the invention, an implant is provided which includes an envelope which defines an interior volume, a fluid contained within the interior volume, and fluid dampening means contained within the interior volume for dampening the propagation of a wave through the fluid.

In accordance with another aspect of the invention, a breast implant is provided which has baffles inside an envelope adapted to contain a fluid material.

In accordance with another aspect of the invention, a breast implant is provided which has multiple chambers and one or more of the chambers, adapted to contain a fluid material, also contains baffles which form and maintain the shape of the chamber and reduce wave or rippling motion of the fluid material contained in the chamber.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

In the annexed drawings:

FIG. 1 illustrates a cross sectional side view of a breast implant with baffles in accordance with the present invention;

FIG. 2 illustrates a cross sectional front view, taken in the direction of arrow 2—2 in FIG. 1, of a breast implant with baffles in accordance with the present invention;

FIG. 3 illustrates a cross sectional side view of a breast implant similar to FIG. 1 with the baffles tethered to the implant envelope;

FIG. 4 illustrates a cross sectional side view of a breast implant with baffles in accordance with the present invention; and FIG. 5 illustrates a cross sectional front view of a multiple chamber breast implant with baffles in accordance with the present invention.

DETAILED DESCRIPTION OF THE PREFERRED EMBODIMENTS

With references to the various figures, and initially to FIG. 1, there is shown a breast implant 10 in accordance with one embodiment of the present invention implanted in a breast as shown generally by phantom lines 11. The breast implant 10 includes a conventional envelope 12 preferably constructed of a biocompatible material, such as a silicone elastomer. Such an envelope 12 typically has a wall of sufficient thickness to provide structural integrity to retain fluids while achieving the desired flexibility and malleability of the implant 10. Examples of suitable envelope materials are Biocell and other materials by McGhan Medical Co.

The envelope 12 defines an interior volume 13 containing a fluid material 14 and fluid dampening material 16 in contact with the fluid. The fluid material 14 and dampening material 16, like the envelope 12, are preferably biocompatible Examples of some suitable fluid materials 14 include saline, silicone gel, and organic oils such as peanut or soybean oil. The dampening material 16 may be of a variety of materials and configurations, as will be more fully discussed below, which will appropriately attenuate the propagation of a fluid wave through interior volume 13 in response to an applied force.

The specific fluid material 14 and dampening material 16 are chosen such that the viscosity and density of the fluid coact with the dampening material to provide the interior volume 13 with the simulated static and dynamic characteristics of natural breast tissue. Consequently, a breast reconstructed or enhanced with the implant 10 will feel like a natural breast and will approximate the movement and feel of a natural breast.

The dampening material 16 may, in one embodiment, be layers of relatively planar sheets or baffles 18. The baffles 18 may be of the same material of which the envelope 12 is made or some other biocompatible material. The baffles 18 can be oriented parallel to the posterior wall 20 of envelope 12 or at any other angle within the envelope depending upon the desired shape, rigidity and malleability of the implant. Any number of baffles can be incorporated into the envelope interior 13 from as few as one to as many as would substantially fill the entire volume of the envelope.

With reference to FIGS. 1 and 2, the baffles 18 are shown in a sequentially enlarging progression from the anterior wall 22 to posterior wall 20 of the envelope 12 thus generally conforming to the interior contours of envelope. For example, baffle 18', near the anterior wall 22 of envelope 12, has a generally circular shape with a diameter less than baffle 18" placed closer to the posterior wall 20 of the envelope. In this manner the baffles 18 provide significant dampening of a fluid wave propagating through the implant, especially from posterior to anterior walls 20, 22 or vice versa. Furthermore, the baffles 18 may be used to provide enhanced dampening and a degree of structural support by being mechanically fixed to the interior walls of envelope 12 such as through the use of tethers 23, as shown in FIG. 3. Selection of certain materials and material thicknesses for the baffles 18 may also provide a degree of structural support to the implant 10.

The baffles 18 may be constructed of a fluid impervious material or a fibrous or porous material which impedes but does not completely prevent flow of the fluid material therethrough. One example of a fibrous material is polyethylene fiber.

With reference to FIG. 4, another type of baffling within a fluid-filled envelope 12 is illustrated which uses generally spherically shaped baffles 24 which, similar to the sheet baffles 18, can be made of biocompatible radiolucent fibrous material which becomes saturated by the fluid material 14 and dampens dynamic wave front motion of the fluid material 14 within the envelope 12 by providing physical obstruction to propagation of such waves. Selection of certain materials for the baffles 24 within the envelope 12 may also provide structural support to the envelope to assist in maintaining the desired shape of the implant 10. The generally spherical baffles 24 may freely float within the volume 13 or one or more of the baffles 24 may be mechanically connected to the interior walls of envelope 12 and/or connected to one another, see, for example, baffles 24' and 24". The spherical baffles 24 act to provide fluid dampening in many directions through the implant 10.

The baffles 24 may substantially fill the interior 13 of the envelope 12 so that the contours of the baffles act to maintain the shape of the implant. The baffles 24 may also be constructed as one continuous baffle having a shape matching the desired shape of the envelope 12.

FIG. 5 illustrates a multi-chamber breast implant 26 employing an alternate fluid dampening system. The internal volume 28 of multi-chamber envelope 30 is subdivided by internal walls 32 into, for example, four separate chambers a, b, c, d. The chamber walls 32 can be made of the same material as envelope 12 and can be molded as a single uniform piece with envelope 12. As shown in chamber a, layered baffles 34 can be made in quarter sections, or sections which otherwise conform to the interior of the chamber a, to dampen the fluid material 14 contained in the chamber in a manner similar to that described with reference to FIG. 1. Baffles 34 may or may not be mechanically attached to one another or to the chamber walls 32 and/or interior walls of envelope 30.

In chamber b there are shown sheet shape baffles 36 oriented within the chamber perpendicular to the illustrated cross-section of the envelope 30 to provide a different direction of fluid dampening and structural support than that achieved by the baffles 34 in chamber a. In fact, the baffles may be oriented in any direction within the chambers to achieve optimum fluid dampening and structural support. As illustrated in chamber c, generally spherical baffles 38 can also be included in one or more of the multiple chambers of the envelope to provide dampening and structural support of the fluid contained,therein in a manner similar to that described with reference to FIG. 4. Further, different fluid materials, for example having differing viscosities or densities, may be used in separate chambers to attribute different fluid characteristics to the different chambers.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the following claims.

What is claimed is:

1. A breast implant comprising an envelope enclosing a chamber containing a fluid material and a plurality of baffles deployed within said chamber, said plurality of baffles only partially restricting the flow of said fluid material within said chamber and wherein each of said plurality of baffles is a unitary body comprising a porous substantially planar sheet.

2. A breast implant comprising an envelope enclosing a chamber containing a fluid material and a plurality of baffles deployed within said chamber, said plurality of baffles only partially restricting the flow of said fluid material within said chamber and wherein each of said plurality of baffles comprises a substantially spherical porous body having a unitary construction.

* * * * *